United States Patent
Ercan

(10) Patent No.: US 10,433,804 B2
(45) Date of Patent: Oct. 8, 2019

(54) DEVICE FOR DYNAMIC CONTROLLING OF THE RADIATION LEVEL FOR RADIATION-BASED, REAL-TIME, MEDICAL-IMAGING SYSTEMS

(71) Applicant: EKIN EFE OZEL SAGLIK HIZMETLERI MEDIKAL TEKNOLOJI AR-GE GIDA INSAAT SAN. TIC. LTD. STI., Izmir (TR)

(72) Inventor: Ertugrul Ercan, Izmir (TR)

(73) Assignee: EKIN EFE OZEL SAGLIK HIZMETLERI MEDIKAL TEKNOLOJI AR-GE GIDA INSAAT SAN. TIC. LTD. STI., Bizmir (TR)

( * ) Notice: Subject to any disclaimer, the term of this patent is extended or adjusted under 35 U.S.C. 154(b) by 125 days.

(21) Appl. No.: 15/516,886

(22) PCT Filed: Jan. 12, 2015

(86) PCT No.: PCT/TR2015/000090
§ 371 (c)(1),
(2) Date: Apr. 4, 2017

(87) PCT Pub. No.: WO2016/114728
PCT Pub. Date: Jul. 21, 2016

(65) Prior Publication Data
US 2018/0271472 A1    Sep. 27, 2018

(30) Foreign Application Priority Data

Jan. 12, 2015 (TR) ................... 2015/00340

(51) Int. Cl.
*A61B 6/00* (2006.01)
*H05G 1/56* (2006.01)
*H05G 1/30* (2006.01)

(52) U.S. Cl.
CPC .............. *A61B 6/542* (2013.01); *A61B 6/467* (2013.01); *H05G 1/56* (2013.01); *H05G 1/30* (2013.01)

(58) Field of Classification Search
CPC ........... A61B 6/00; A61B 6/542; A61B 6/486; A61B 6/487; A61B 6/54; A61B 6/548; H05G 1/56
USPC .................... 378/42, 114, 115, 117
See application file for complete search history.

(56) References Cited

U.S. PATENT DOCUMENTS

| 6,368,269 B1 | 4/2002 | Lane |
| 2007/0183574 A1 | 8/2007 | Morehead |
| 2011/0295191 A1 | 12/2011 | Injev |
| 2012/0163534 A1 | 6/2012 | Nambu |

*Primary Examiner* — Jurie Yun
(74) *Attorney, Agent, or Firm* — Crose Law LLC; Bradley D. Crose

(57) ABSTRACT

The invention is a device for controlling the amount of radiation emitted during the process of imaging, particularly by instruments capable of radiation-based real-time imaging, such as fluoroscopy and cine acquisition. The related device comprises a pressure-sensitive foot controller (1), a pressure sensor (2), a signal transmitter (3), a signal converter (4), and signal processing software (5). The invention enables real-time controlling of the image quality and the image frame rate by means of a foot-switcher with the new function of being driven by a pressure-sensitive controller.

4 Claims, 1 Drawing Sheet

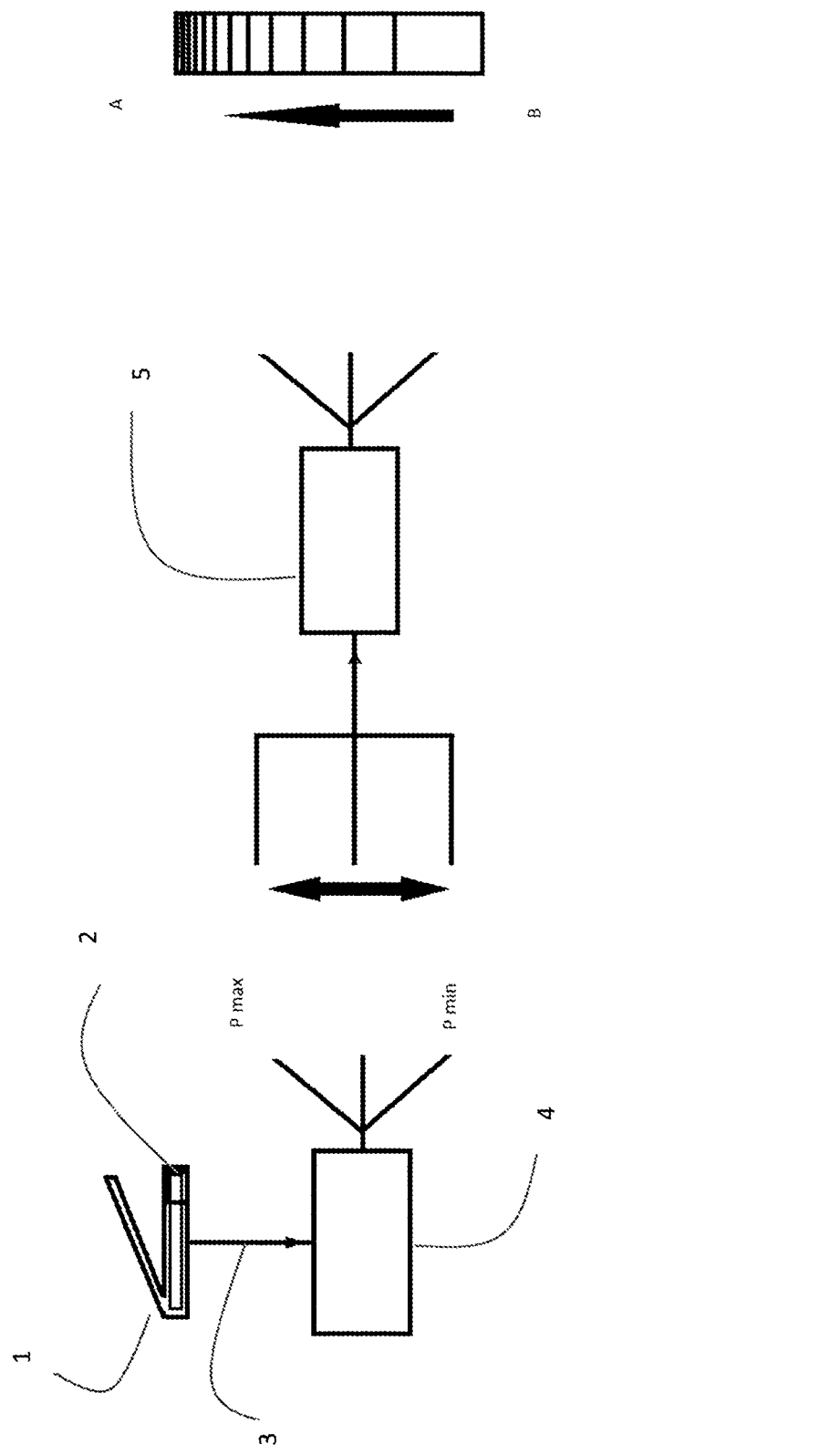

DEVICE FOR DYNAMIC CONTROLLING OF THE RADIATION LEVEL FOR RADIATION-BASED, REAL-TIME, MEDICAL-IMAGING SYSTEMS

DESCRIPTION OF THE INVENTION

The invention is a device for checking the amount of radiation emitted during the imaging process, particularly by devices capable of radiation-based real-time imaging, such as fluoroscopy and cine acquisition. The invention is particularly suitable for use by cardiologists and radiologists performing angiographic interventions in the field of medicine. The invention enables real-time controlling of the image quality and the image frame rate by means of a foot-switcher with the new function of being driven by a pressure-sensitive controller.

PRIOR ART

Fluoroscopy and cine acquisition are angiographic medical imaging techniques used for obtaining real-time radiological images of the patient.

In its simple form, a fluoroscope comprises an X-ray source and fluorescent display between which the patient is placed. In modern fluoroscopes, the display is connected to an X-ray concentrator and a video camera that enables monitoring or recording of the images on the display. The basic source of imaging for fluoroscopes is the X-ray source. X-rays, on the other hand, emit a high amount of radiation.

Cine acquisitions are radiation-based, real-time motion image records. As cine acquisition is performed by taking multiple-image sections that require radiation at short time intervals, it emits a very high amount of radiation compared to flouroscopy. The frequency of the section forming the movie is defined as the "frame rate".

As the basic source forming the image in the mentioned systems is radiation, the image quality increases as the amount of radiation is increased.

Under all conditions, the choice of the operator performing the operation is to keep the radiation amount, that is to say the image quality, high. However, high amounts of radiation capable of providing high quality images are harmful to the patient, operator and technicians.

This situation necessitates a balance between the risks that the patient is subject to radiation emitted by the concerned systems and the benefit to be derived. While the high amount of radiation used improves the image quality, it might lead to various radiation-based diseases in the patient and the operator, such as cancer. On the other hand, because keeping the radiation amount at low levels reduces image quality, this might lower the performance of the operation applied by the operator.

Today, fluoroscopy and computerized tomographic imaging methods are the most powerful means by which medical-based X-rays are received by patients. The majority of fatal cancer cases experienced in the USA are caused by accumulation of medical X-rays in the patient's body. Such disorders are gradually increasing due to increased use of medical radiation in the USA.

In the prior art, devices capable of performing radiation based on real-time imaging, such as fluoroscopy and cine acquisition and suchlike, lack the means to effectively control the radiation amount during the process. When initiating the operation, the radiation level is set by means of a controller and radiation is applied to the patient during the process without effectively controlling the level.

Available devices are operated by a footswitch. The device operates by switching on the radiation upon activation of the footswitch and switching off the radiation upon release of the footswitch. The frame frequency of the radiation images remains constant during the process for each exposure.

In this case, the operator prefers a high level of frame frequency in order to ensure maximum image quality and improve the chances of success of the operation; thus, the operator prefers to work with more severe radiation amounts.

However, as the footswitch used in existing systems has no control function other than turning the device on and off, it is not suitable for applying differing radiation regimes according to the needs of different patients.

Furthermore, working with a fixed frame rate during the operation and imaging process causes not only the patient but also the operator performing the operation to receive high doses of radiation.

Systems used in the prior art enable the operator to manually modify the frame rate applied during operation, although only to a limited degree. However, it is not practical for the operator to continuously modify the frame rate applied during the taking of each film, thereby interrupting the applied process, and thus is not suitable. This fact necessitates systems that enable the operator to modify the radiation dose non-manually.

Some methods are contemplated in the prior art for reducing and limiting the amount of radiation to the patient and the operator; however, these methods have proved to be insufficient. For instance, storing the last image recorded, while the operator performs an operation over such an image, is one possible example. However, this solution can only be employed under conditions where the device is used for imaging purposes but cannot be employed where the device is used for an imaging function assisting an operation. Another method is to check the amount of radiation accumulated on the skin by constantly measuring the radiation dose received by the patient. However, this method enables involves measuring the amount of radiation dose received by the patient, and the imaging operation might be interrupted when the dose increases.

In European patent application No. EP1181897, a surgery navigation and imaging system which accommodates a fluoroscope is disclosed. However, no structure associated with checking the radiation generated by the fluoroscope during surgery is disclosed within the system.

In application No. EP2783633 (A1), a system for checking and minimizing the radiation of imaging devices used in medical and other sectors through radiation is disclosed. The concerned system aims to eliminate the harmful effects of radiation on the operator operating the system. It is not possible to control the radiation received by the patient by use of this system.

In the system specified in the application, the operator is protected by formation of a safe zone with decreased radiation amount. However, if this application is used in any medical imaging system, it is not possible to protect the patient, as the amount of radiation received by the patient is not regulated.

Another example in the prior art relates to a fluoroscope accommodating multiple control mechanisms, as disclosed in patent application No. US2007183574. In this application, the fluoroscope is controlled by both a footswitch mechanism and a visually-sensitive goggle mechanism. The fluoroscope precludes giving off radiation to the patient as long as the operator does not look at the monitor used for observing the process, and the fluoroscope is activated and the image is formed only after the operator looks at the monitor.

The mechanism aims to reduce the amount of total radiation received by the patient by deactivating the fluoroscope when necessary. However, the fact that the operator generates X-rays by activating the fluoroscope by looking causes the system to function slowly. This increases overall operation time. Moreover, use of the concerned mechanism has no effect on frame rate during cine acquisition or fluoroscopy for reducing the amount of radiation.

Another technical deficiency of the mentioned device is that continuous activation and deactivation of the x-ray source will damage the fluoroscope over time. This reduces the service life of the fluoroscope.

OBJECT OF THE INVENTION

The object of the invention is to propound a system that reduces and limits the total amount of radiation received by the patient by checking the total amount of radiation received by the patient through a control mechanism.

Another object of the invention is to create a safer imaging environment for the operator by limiting the amount of radiation received by the operator.

Another object of the invention is to propound a system that enables increasing the amount of radiation, and thus image quality, in cases that require high resolution.

Another object of the invention is to enable adjustment of the image quality at any time during the operation under the control of the operator, thus propounding a more effective system capable of swifter operation.

Another object of the invention is to propound a system where the radiation dose can be adjusted dynamically; thus it is capable of eliminating operation errors and defects that might arise due to low resolution.

Another object of the invention is to propound a system where the operator is able to adjust and continuously increase and decrease the radiation dose non-manually.

Another object of the invention is to propound a radiation dose regulation system suitable for installation in existing devices, capable of radiation-based real-time imaging, such as fluoroscopy and cine acquisition.

Another object of the invention is to propound a system where the operator is able to adjust and continuously increase and decrease the image frame rate non-manually.

Another object of the invention is to enable the operator to modify the image frame rate dynamically during fluoroscopy and cine acquisition.

DESCRIPTION OF FIGURES

FIG. 1. Mechanism showing dynamic control of device capable of radiation-based real-time imaging.

The parts illustrated in FIG. 1 are enumerated individually. The part names corresponding to such numbers are as follows:
1. Controller
2. Pressure sensor
3. Signal transmitter
4. Signal converter
5. Encoder
A. High quality image
B. Low quality image
Pmax. High pressure
Pmin. Low pressure

DESCRIPTION OF THE INVENTION

The invention discloses a system or device that enables controlling the radiation dose, and thus the image quality and the image frame rate, generated by devices capable of radiation-based real-time imaging, such as fluoroscopy and cine acquisition, by means of a foot-activated pressure-sensitive controller.

The present invention can not only be used for providing measured pressure command, thereby controlling image quality and frame rate by installing additional apparatus to devices capable of radiation-based real-time imaging, such as fluoroscopy and cine acquisition, currently available in the prior art, but also the entire system can be designed in advance for control of a new device.

The present invention comprises a pressure-sensitive foot controller (1); a pressure sensor (2) capable of detecting the intensity of the pressure-based commands transferred to the controller (1); a signal transmitter (3) that transmits the analog commands detected by the pressure sensor (2) outside the controller (1); a signal converter (4) capable of converting analog data from the pressure sensor (2) into numerical values; and an encoder (5) capable of regulating the dose of radiation emitted by transmitting the pressure command corresponding to the image property to the device capable of radiation-based real-time imaging, and by converting numerical values from the signal converter (4) to corresponding image properties such as image quality and frame rate.

All of the aforementioned parts of the invention can be installed onto a newly developed radiation-based real-time imaging device in order to realize the objects of the invention, and the technical solutions aimed at by the invention can also be fulfilled by installing some or all of the parts into a previously-produced device.

The aforementioned foot controller (1) is in the form of a footswitch in an embodiment of the invention. However, the invention is suitable for use with all kinds of foot-operated devices capable of receiving foot-activated pressure commands.

The signal transmitter (3) of the invention can be a coaxial cable or a shielded twisted pair (STP). In this manner, the effect of electrical noise on signals that might arise from external conditions is minimized.

The image can be generated by the encoder (5) in a range from high quality image (A) to low quality image (B), corresponding to pressure values occurring in the high pressure (Pmax) and low pressure (Pmin) range applied by the operator to the foot controller (1).

The invention is suitable for use in cases where the device capable of radiation-based real-time imaging performs the imaging operation for managing an operation. The most important example of this type of operation is angiographic operations. In an embodiment of the invention, while high quality image (A) is 30 frame/sec, low quality image (B) is 1 frame/sec.

For instance, when, during an angiographic operation, the operator is placing and advancing the wire to the aorta, as he does not require a high resolution image, the operator shall keep the pressure low on the controller (1), thereby working with lower quality image, but when a more accurate image is required for stent implantation, etc., the operator shall increase the pressure on the controller (1) to improve the image quality and increase the frame rate.

In this case, the operator can modify the amount of radiation instantly during the operation and shall not treat the patient with additional unnecessary radiation; further, the operator is capable of increasing image quality when he needs high quality image In addition, as the operator is capable of performing all such operations with their foot, and is not using their hands, there will be no impediment to his hands when setting the radiation level.

The invention claimed is:

1. A device for dynamic controlling image quality and frame rate for use in radiation-based real-time imaging devices, characterized by comprising a pressure-sensitive foot controller (1) that enables reception of foot-activated pressure, a pressure sensor (2) that detects pressure-based data transferred to the controller, a signal transmitter (3) that transmits the data received from the pressure sensor (2) to signal converter (4) a signal converter (4) that converts the data received from the signal transmitter (3) into numerical values, an encoder (5) comprising a signal processing software that forms images in the range of a high quality image (A) and a low quality image (B) with respect to the pressure-based data received from the controller (1) by converting the numerical values received from the signal converter (4) into image quality and frame rate values and by transmitting the image quality and frame rate values to a radiation-based real-time imaging device.

2. A device for dynamic controlling image quality and frame rate according to claim 1, characterized in that the foot controller (1) is in the form of a footswitch.

3. A device for dynamic controlling image quality and frame rate according to claim 1 characterized in that the high quality image (A) is 30 frame/sec.

4. A device for dynamic controlling image quality and frame rate according to claim 1 characterized in that the low quality image (B) is 1 frame/sec.

* * * * *